(12) United States Patent
Compton et al.

(10) Patent No.: US 11,141,914 B2
(45) Date of Patent: Oct. 12, 2021

(54) THREE-DIMENSIONAL PRINTING SYSTEM

(71) Applicant: Genesis Dimensions, LLC, Houston, TX (US)

(72) Inventors: James Eric Compton, Conroe, TX (US); Casey Roberts, Houston, TX (US); Ben Steinhauer, Houston, TX (US); Kaleb Steinhauer, Houston, TX (US); Daniel Holman, Houston, TX (US)

(73) Assignee: Genesis Dimensions, LLC, Houston, TX (US)

( * ) Notice: Subject to any disclaimer, the term of this patent is extended or adjusted under 35 U.S.C. 154(b) by 224 days.

(21) Appl. No.: 15/656,407

(22) Filed: Jul. 21, 2017

(65) Prior Publication Data

US 2018/0022026 A1    Jan. 25, 2018

Related U.S. Application Data

(60) Provisional application No. 62/365,130, filed on Jul. 21, 2016.

(51) Int. Cl.
*B29C 64/209* (2017.01)
*A61B 34/30* (2016.01)
*B29C 64/118* (2017.01)
*B29C 64/20* (2017.01)
*B29C 64/188* (2017.01)
*B29C 64/106* (2017.01)
(Continued)

(52) U.S. Cl.
CPC ............ *B29C 64/209* (2017.08); *A61B 34/30* (2016.02); *B29C 64/106* (2017.08); *B29C 64/118* (2017.08); *B29C 64/188* (2017.08); *B29C 64/20* (2017.08); *B29C 64/336* (2017.08); *B29K 2075/00* (2013.01); *B29K 2105/04* (2013.01); *B29K 2995/0063* (2013.01)

(58) Field of Classification Search
CPC ... B29C 64/209; B29C 64/106; B29C 64/336; B29C 64/188; B29C 64/118; B29C 64/20; A61B 34/30; B29K 2075/00; B29K 2995/0063; B29K 2105/04
See application file for complete search history.

(56) References Cited

U.S. PATENT DOCUMENTS

| | | | |
|---|---|---|---|
| 1,579,972 A * | 4/1926 | Thoresen | B43L 23/006 30/462 |
| 9,433,969 B2 * | 9/2016 | Pridoehl | B33Y 30/00 |

(Continued)

FOREIGN PATENT DOCUMENTS

EP    1579972 A2 *  9/2005  .......... B29C 44/445

OTHER PUBLICATIONS

Rammer (EP 1579972) English Translation from Espacenet (Year: 2004).*
EP-1579972-A2 Translation from WIPO Patentscope (Year: 2021).*

*Primary Examiner* — Francisco W Tschen
*Assistant Examiner* — Guy F Mongelli
(74) *Attorney, Agent, or Firm* — Polsinelli PC

(57) ABSTRACT

A three-dimensional printing system including at least one positioning mechanism, and at least one end effector movably connected to the at least one positioning mechanism. The at least one end effector includes at least one mixing head configured to dispense a material, and at least one subtractive tool configured to subtract at least a portion of the material such that a desired design is achieved.

13 Claims, 5 Drawing Sheets

(51) Int. Cl.
*B29C 64/336* (2017.01)
*B29K 105/04* (2006.01)
*B29K 75/00* (2006.01)

(56) References Cited

U.S. PATENT DOCUMENTS

| | | | | |
|---|---|---|---|---|
| 9,566,742 | B2 | 7/2017 | Keating et al. | |
| 2002/0019683 | A1* | 2/2002 | White | B33Y 50/02 700/255 |
| 2010/0191360 | A1* | 7/2010 | Napadensky | G06T 17/00 700/98 |
| 2013/0295338 | A1* | 11/2013 | Keating | B28B 19/003 428/174 |
| 2014/0079841 | A1* | 3/2014 | Pridoehl | B29C 64/314 425/375 |
| 2014/0284832 | A1* | 9/2014 | Novikov | B29C 64/393 264/40.1 |
| 2015/0140147 | A1* | 5/2015 | Konstantinos | B29C 64/20 425/174 |
| 2015/0147421 | A1* | 5/2015 | Te | B28B 1/001 118/302 |
| 2015/0352790 | A1* | 12/2015 | Hadas | B29C 64/118 700/119 |
| 2016/0101546 | A1* | 4/2016 | Gneuss | B29C 44/60 264/53 |
| 2016/0151833 | A1* | 6/2016 | Tsao | B33Y 30/00 65/60.1 |
| 2017/0157815 | A1* | 6/2017 | Volpato | B29C 44/30 |
| 2017/0306171 | A1* | 10/2017 | Vidavsky | C09D 11/101 |
| 2017/0321028 | A1* | 11/2017 | Dougherty | B32B 17/04 |
| 2019/0021796 | A1* | 1/2019 | Timperley | A61B 34/70 |

\* cited by examiner

THREE-DIMENSIONAL PRINTING SYSTEM

CROSS REFERENCE TO RELATED APPLICATIONS

This is a non-provisional application based upon U.S. provisional patent application Ser. No. 62/365,130, entitled "THREE-DIMENSIONAL PRINTING SYSTEM", filed Jul. 21, 2016, which is incorporated herein by reference.

BACKGROUND OF THE INVENTION

1. Field of the Invention

The present invention relates to three-dimensional printing, and, more particularly, to 3D printing and surface finishing of plural component material molds or objects.

2. Description of the Related Art

Three-dimensional (3D) printing, also known as rapid or additive manufacturing, is a class of manufacturing that allows for the production of physical three-dimensional objects based from computer design data. Generally, methods of additive manufacturing technology employ the use of a 3D printer to extrude a given material layer-by-layer to construct an intricate 3D object. The layer-by-layer process may also create a 3D object which is aesthetically unpleasing. 3D printing has numerous advantages over traditional manufacturing, which can lead to a more cost-effective and rapid method of manufacturing.

Although 3D printing has numerous advantages, at times the process of 3D printing renders the 3D object unfit. The layer-by-layer process can create a 3D object with an undesirable surface finish. Further, in printing with certain materials a 3D object may be structurally unsound or impractical to manufacture if it was to be created solely through an additive process. 3D printing with a plural component material is not Sui generis when it comes to the above-mentioned pitfalls; it suffers from the same issues, which can often lead to 3D objects that cannot practically be used in subsequent manufacturing.

What is needed in the art is a cost-effective system and method for printing and surface finishing a mold.

SUMMARY OF THE INVENTION

The present invention provides a 3D printing system and method for producing a quick curing, plural component material mold by using additive and subtractive measures according to computer design data.

The present invention in one form is directed a three-dimensional printing system including at least one positioning mechanism, and at least one end effector movably connected to the at least one positioning mechanism. The at least one end effector includes at least one mixing head configured to dispense a material, and at least one subtractive tool configured to subtract at least a portion of the material such that a desired design is achieved.

The present invention in another form is directed to a three-dimensional printing system. The three-dimensional printing system includes a first positioning mechanism, a second positioning mechanism associated with the first positioning mechanism, and a first end effector movably connected to the first positioning mechanism. The first end effector includes at least one nozzle which is configured for dispensing a material layer-by-layer to form a mold. The three-dimensional printing system further includes a second end effector movably connected to the second positioning mechanism. The second end effector includes at least one subtractive tool which is configured for subtracting at least a portion of the mold.

The present invention in yet another form is directed to a method for 3D printing. The method includes the steps of providing a three-dimensional printing system. The three-dimensional printing system includes at least one positioning mechanism, and at least one end effector movably connected to the at least one positioning mechanism. The at least one end effector includes at least one mixing head configured to dispense a material, and at least one subtractive tool configured to subtract at least a portion of the material. The method includes the further steps of depositing the material by the nozzle layer-by-layer to form a mold, and subtracting the material by the subtractive tool to subtract at least a portion of a surface of the material in order to achieve a desired design on the mold.

An advantage of the present invention is that a plural component material mold can be cost-effectively and readily created according to an intricate computer design model.

Another advantage of the present invention is that at least one mixer may dynamically alter various properties of the plural component material mold during operation of the three-dimensional printing system.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DESCRIPTION OF THE INVENTION

Figure 1:
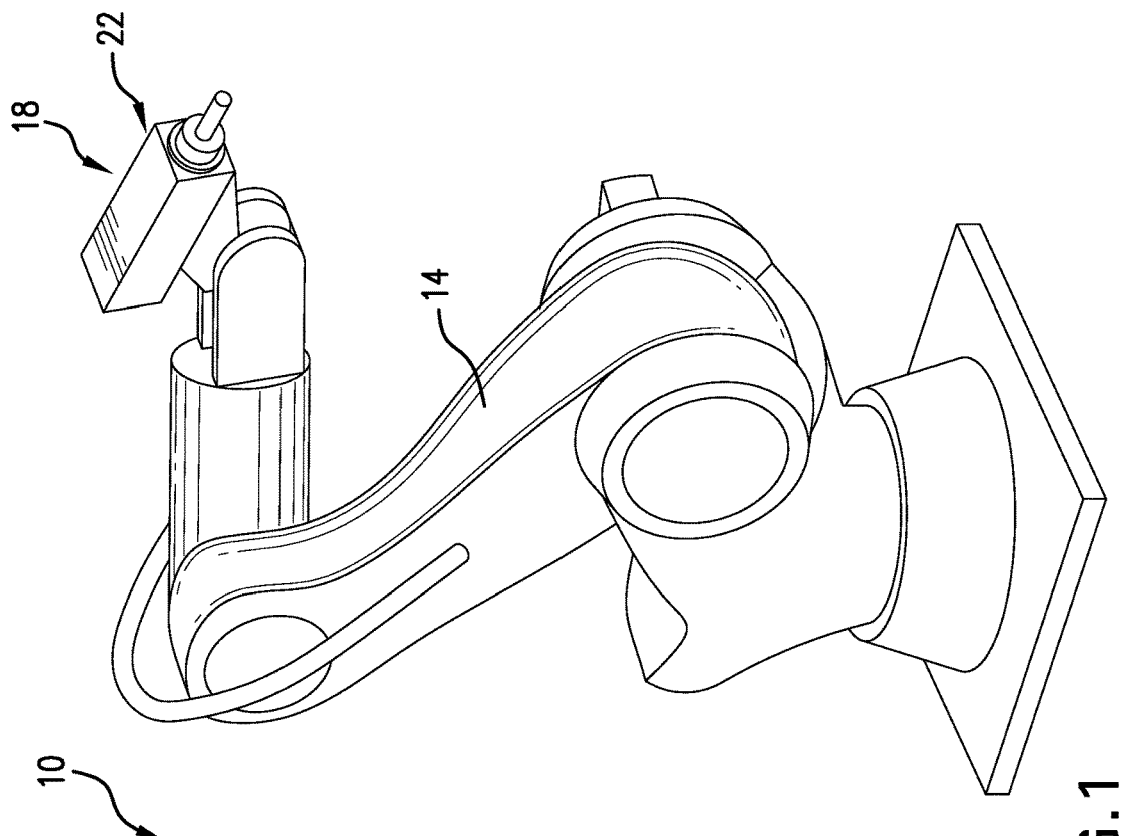
FIG. 1 is a perspective view illustrating the 3D printing system according to the present invention.
Figure 1:
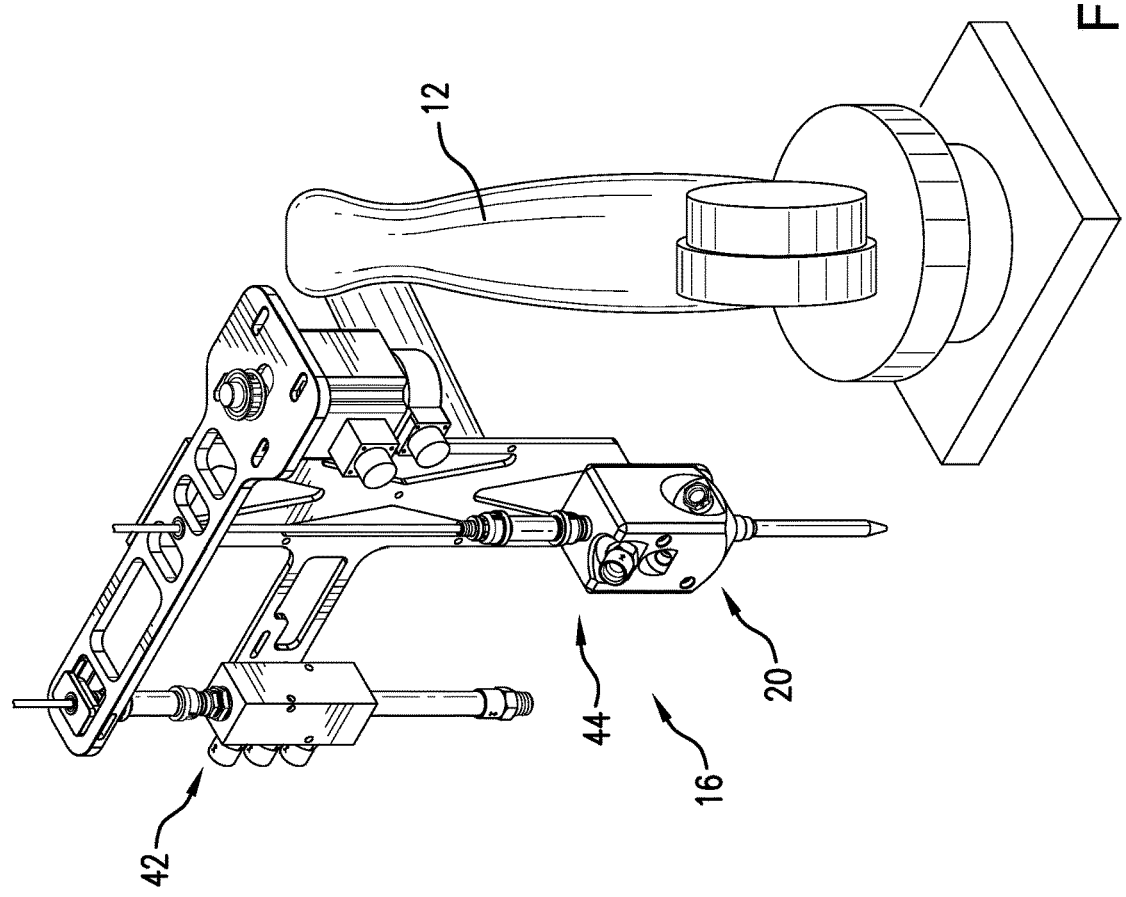

Referring now to the drawings, and more particularly to FIG. 1, there is shown an embodiment of a three-dimensional (3D) printing system 10 that includes at least one positioning mechanism 12, 14, and at least one end effector 16, 18 that is movably connected to the at least one positioning mechanism 12, 14. The at least one end effector 16, 18 may include at least one mixing head 20 and at least one subtractive tool 22. The three-dimensional printing system 10 may be configured for 3D printing a urethane material, such as a plural component material. The three-dimensional printing system 10 may be configured to produce a 3D object 24 (FIG. 7) by an additive and subtractive process.

The three-dimensional printing system 10 may include one or more positioning mechanism(s) 12, 14. In the embodiment of a single positioning mechanism, the positioning mechanism may include an end effector that has a first end in connection with the mixing head 20, and a second end in connection with the milling tool 22. Thereby, the mixing head 20 and the milling tool 22 may be mounted to the respective ends of a single end effector. The single end effector may orient the mixing head 20 and milling tool 22 for a given application. The single positioning mechanism may also have an end effector that mounts a plurality of mixing heads 20 and/or milling tools 22. For example, additional mixing heads 20 may be used to spray or pour other plural chemical component materials.

In another embodiment, three-dimensional printing system 10 may include a first and a second positioning mechanism 12, 14. The positioning mechanisms 12, 14 may respectively have end effectors 16, 18 which include the mixing head 20 and the subtractive tool 22. It should be appreciated that the positioning mechanisms 12, 14 may be located proximate to one another along a fabrication line or the positioning mechanisms 12, 14 may be located spatially distant from one another, for example, the processes of 3D printing plural component material and subtracting the plural component material may occur in separate locations.

The positioning mechanism(s) 12, 14, as shown in the present embodiment, may be in the form of robotic arm(s). Each robotic arm 12, 14 may have an end to which the single or respective end effector 16, 18 is moveably connected. Additionally, the one or more positioning mechanism(s) 12, 14 may be secured to the floor, a gantry, vehicle, track, or drone. It is possible to use a large boom in conjunction with the positioning mechanism(s) 12, 14, which may additionally include a positioning system to assist the deposition of material, in order to create a desired 3D object. Further, it also possible to use a single positioning mechanism 12 or a plurality of positioning mechanisms 12, 14. For example, the use of swarm manufacturing may be employed in which numerous robotic arms are used to create the desired 3D object (not shown).

The first and second end effectors 16, 18 may be movably coupled to the robotic arms 12, 14, respectively, by couplings known in the art. The orientations of the end effectors 16, 18, and thereby the mixing head 20 and subtractive tool 22, may be mechanically or automatically positioned by a control unit in order to produce the desired 3D object 24. One or both of the end effector(s) 16, 18 may also mount a plurality of mixing heads 20 and/or subtractive tools 22. For example, additional mixing heads 20 may be used to spray or pour other plural chemical component materials. It is also possible to have an end effector which includes a positioning system mounted to it in order to provide real-time feedback of location, flow rate, current condition and position of the mixing head 20 or subtractive tool 22, and atmospheric conditions.

Figure 3:
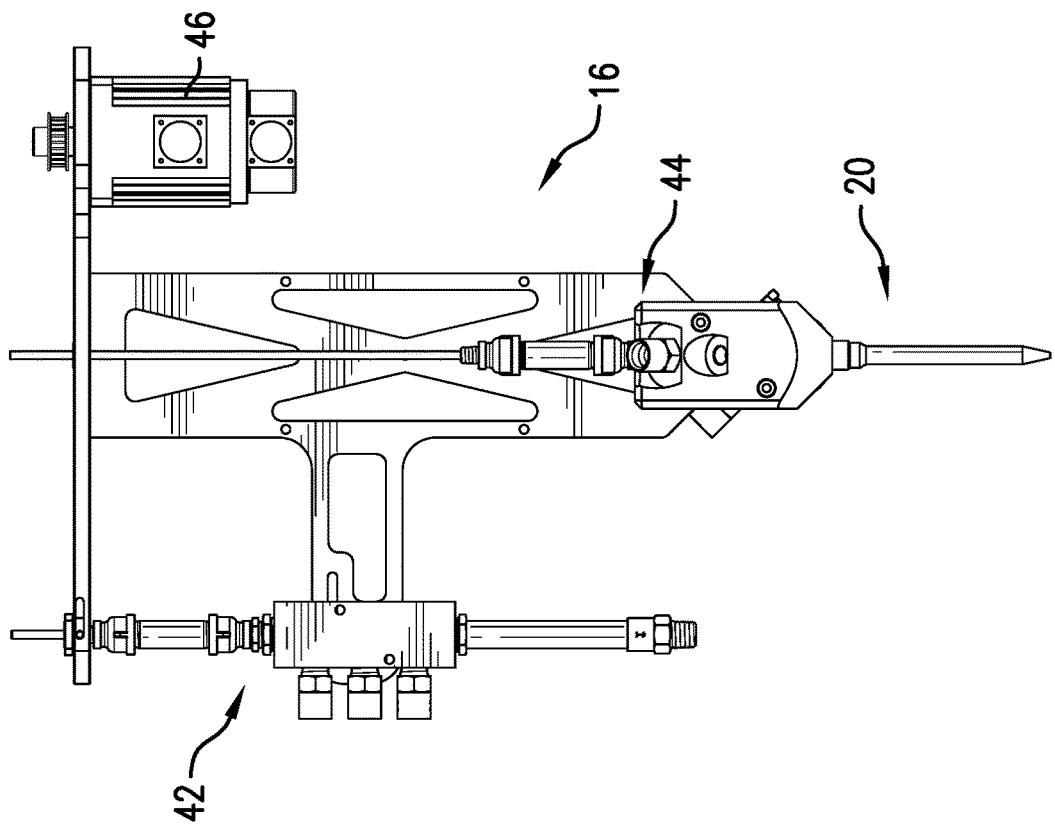
FIG. 3 is a front view illustrating the end effector as shown in FIG. 2.
Figure 2:
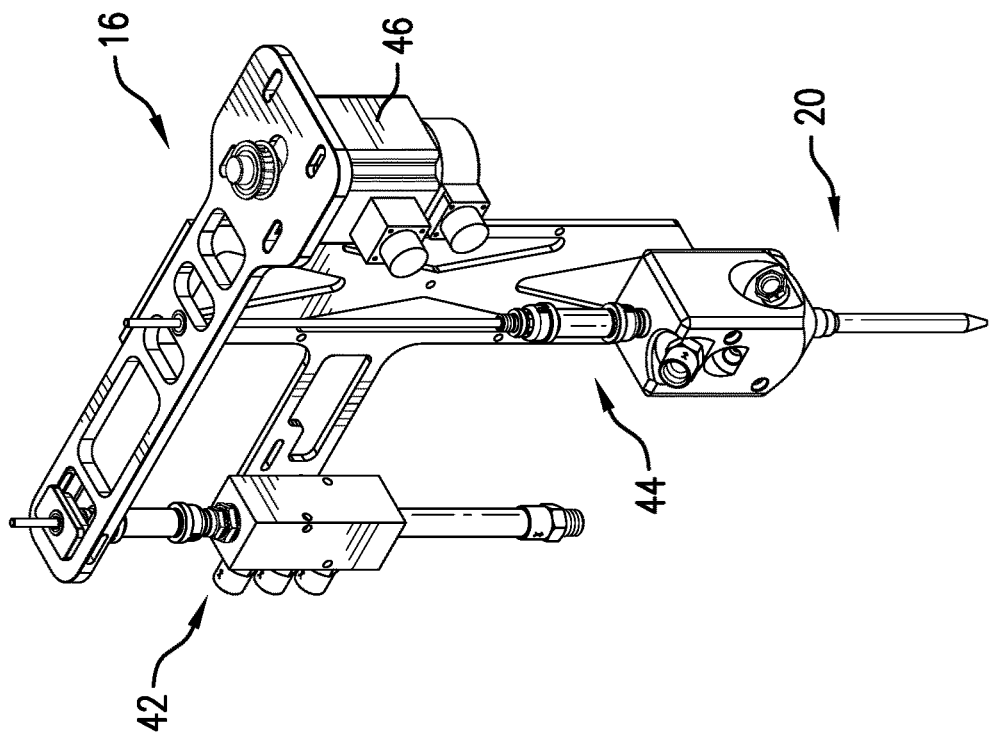
FIG. 2 is perspective view illustrating an end effector of the 3D printing system.
Figure 7:
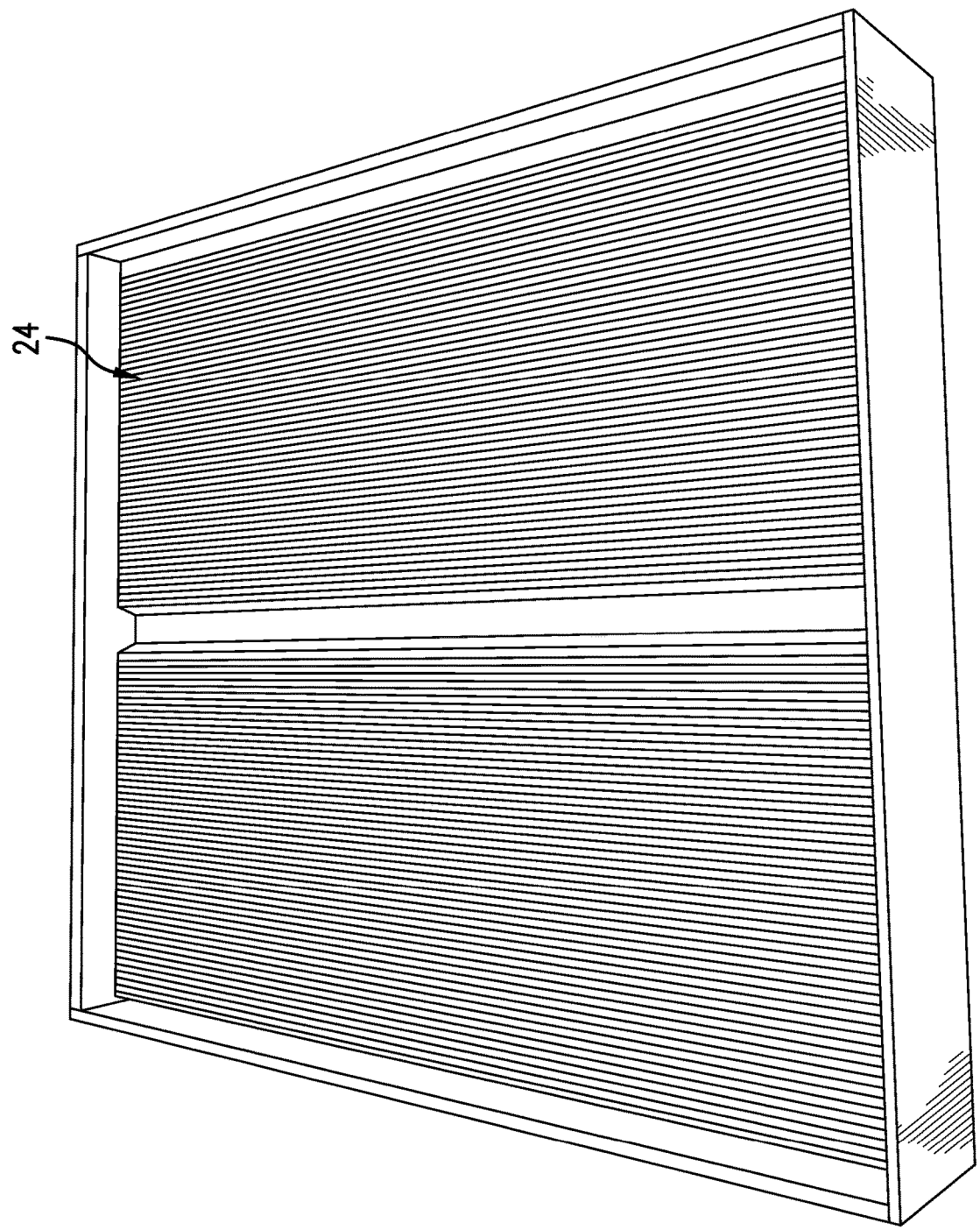
FIG. 7 is a perspective view illustrating a 3D printed mold according to the present invention.

Referring now collectively to FIGS. 1-3, there is shown the first end effector 16. The at least one mixing head 20 of the end effector 16 may be configured to dispense a plural component material layer-by-layer to form the mold 24 (FIG. 7). The material may consist of single or plural components. For example, the material may be composed of at least two components including an activator mixture and a resin mixture. Additionally, for example, the material may be in the form of a foam. If the material is composed of plural components, then the mixing head 20 may be configured to mix the material and dispense the material. The mixing head 20 may be in the form of a purge gun, such as an air pressurized, hydraulic, mechanical, or solvent purge spray gun. The mixing head 20 may also be in the form of a spray or pour nozzle 20.

Figure 4:
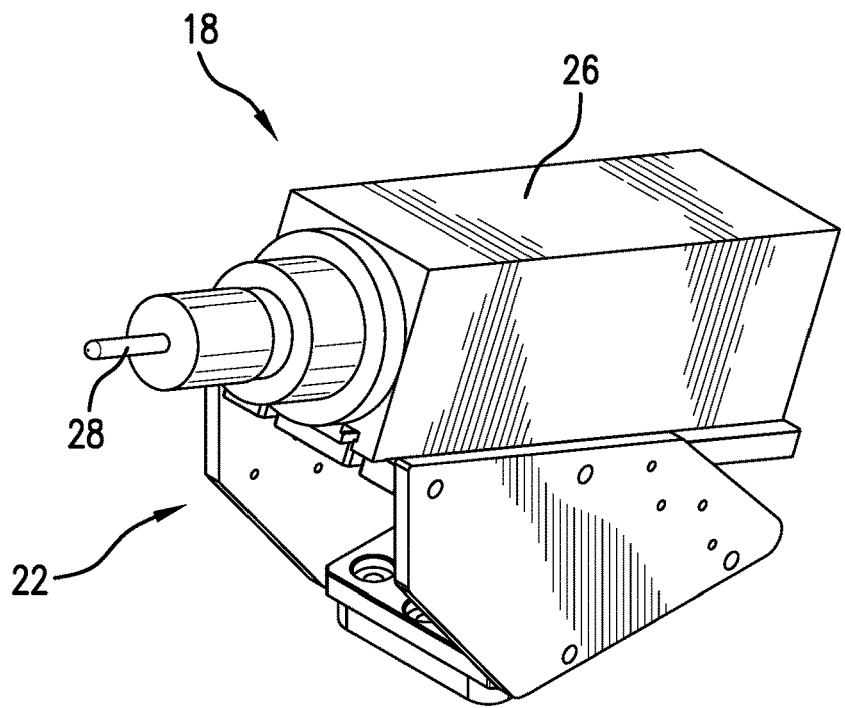
FIG. 4 is a perspective view of another end effector of the 3D printing system.
Figure 5:
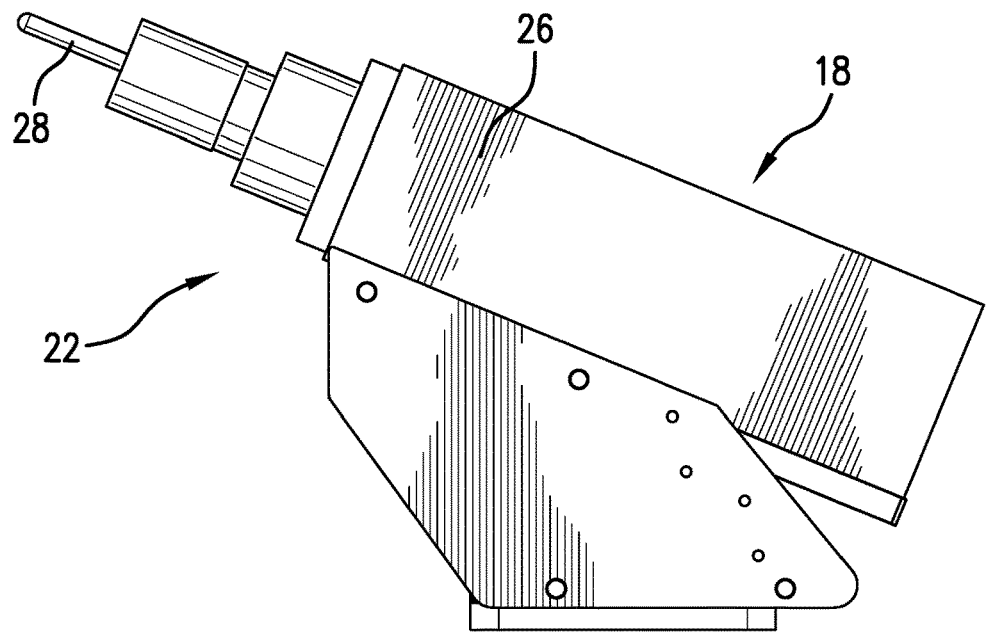
FIG. 5 is a side view of the end effector as shown in FIG. 4.

Referring now to collectively to FIGS. 1 and 4-5, there is shown the subtractive tool 22 of the end effector 18. The at least one subtractive tool 22 is configured to subtract at least a portion of the material after it has been printed by the mixing head 20. For example, the least one subtractive tool 22 may be configured to subtract at least a portion of the material from a surface of the mold 24 such that a desired design is achieved in the surface of the mold 24. The subtractive tool 22 may also be configured for cutting out entire sections of the mold 24. The subtractive tool 22 may be in the form of a milling tool 22. The milling tool 22 includes a motor 26 and an end-milling tool in the form of a drill bit 28. The milling tool 22 may be air or water-cooled. If the milling tool 22 is water-cooled, a cable for water-cooling may be bundled in an existing hose assembly of a mixing head (not shown). Other types of end-milling tools may also be used, including various bits, lasers, air or water jets, sanders, etc. to shape or alter the 3D object 24. The various end-milling tools may be manually or automatically interchanged during a given application.

Figure 6:
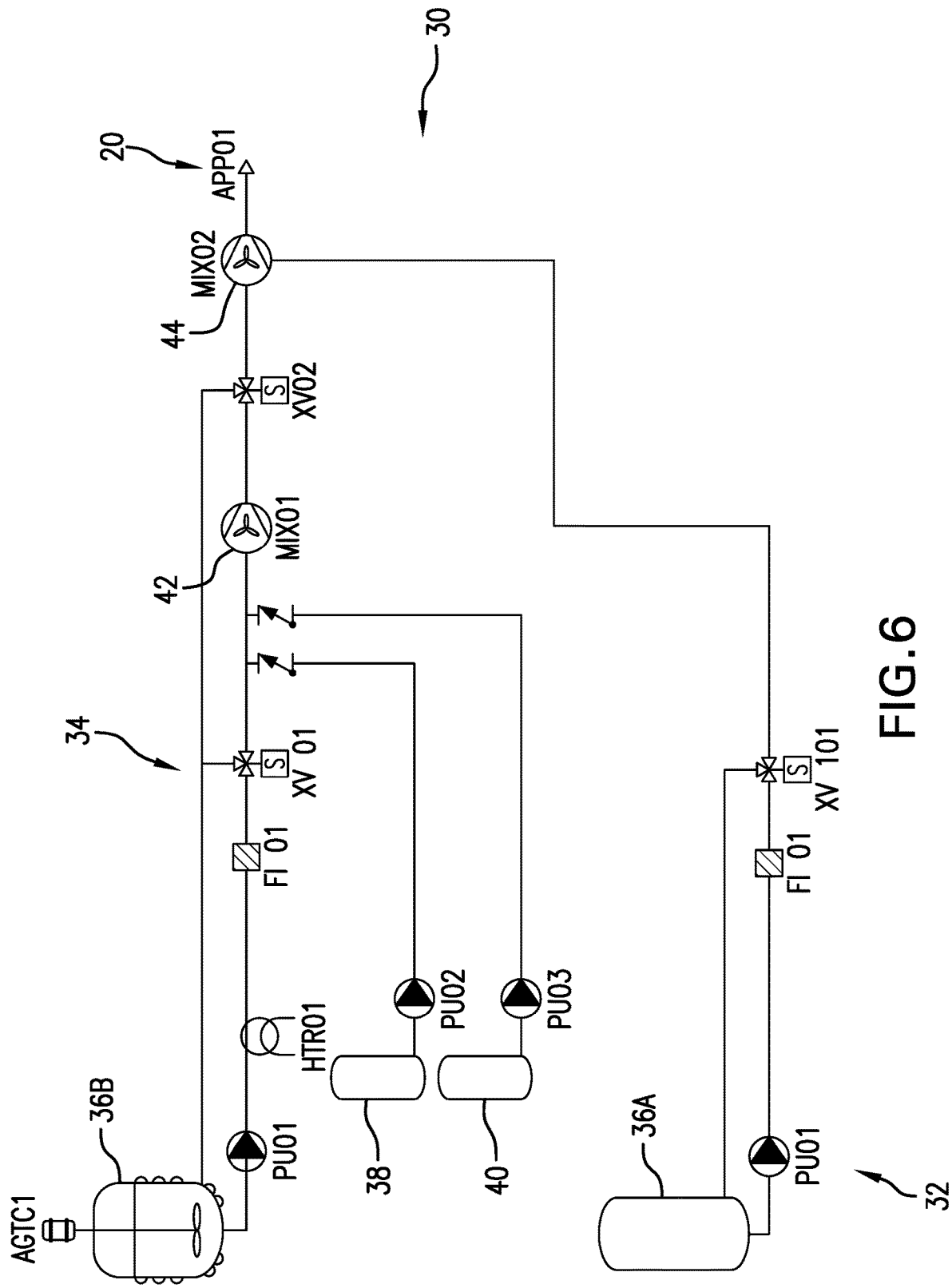
FIG. 6 illustrates a schematic of the chemical component proportioning system.

Referring now to FIG. 6, there is shown a chemical component proportioning system 30 that may be operably coupled to the at least one mixing head 20 and configured to heat, pressurize, and proportion the material. The proportioning system 30 may include one or more reservoirs, which may heat and pressurize the one or plural component material. Additionally, the proportioning system 30 may include various reservoirs, pumps to move the fluid from the reservoirs, valves, heaters, and hoses.

In the present embodiment, the material is a plural component material and the proportioning system 30 includes two subsystems, for example, an A component system 32 and a B component system 34 for respectively storing, heating, transporting and/or proportioning an A component and/or a B component. The proportioning system 30 pressurizes each component of the material to a designated psi, and the proportioning system 30 provides a desired ratio of the components A and B of the material. Also, the proportioning system 30 may provide real-time feedback of various chemical characteristics including viscosity, flow rate, pressure, temperature, etc.

The A and B components may together comprise the material (e.g. a foam). The A component may be an activator mixture and the B component may be a resin mixture. For example, the A component may be in the form of an isocyanate mixture, and the B component may be in the form of a polymer, e.g. a urethane, mixture. The B component may include an accelerant for curing the material and a blowing agent, e.g. water, for controlling the density and strength of the material.

The A and B component system 32, 34 may each include a single reservoir 36A, 36B for housing the respective A and B components. For example, the single reservoir 36B of the B component system 34 may house both of the accelerant and blowing agent. Additionally or Alternatively, the B component system 34 may include two respective reservoirs 38, 40 for individually housing the accelerant and blowing agent (FIG. 6). In this regard, the reservoirs 38, 40 may selectively provide the accelerant and/or blowing agent via pumps in order to alter the various chemical properties of the material. For example, the proportioning system 30 may selectively adjust the blowing agent depending upon a desired density of the material such that a material density of at least a first portion of a first layer of material is different than a material density of at least a second portion of a second layer of material. Further, the density and other material properties may be adjusted within a given layer such that a first portion within a layer has a different density than a second portion within the same layer. Thereby, the density of the material may be altered, for example between approximately 7-60 pounds per cubic foot, in certain layers or sections of the mold 24 in order to provide for a single mold 24 which may accommodate various load demands.

In another embodiment, the proportioning system 30 may further include an electronic control unit (ECU) and mixers 42, 44. The ECU may be configured for selectively controlling the A and B component systems 32, 34. The ECU may be operably coupled to the reservoirs and/or pumps of each system and/or to the mixers 44, 46 in order to proportion the A and B components. Additionally, the ECU may selectively adjust the accelerant and/or the blowing agent of the B component. The ECU may be in the form of any desired control unit or processor.

The first mixer 42 may be configured for mixing the accelerant and blowing agent of the B component. The first mixer 42 may be fluidly connected to the second mixer 44 and located upstream of the nozzle 20. The second mixer 44 may be configured for mixing the A and B components from each system 32, 34. The second mixer 44 may be fluidly connected to the nozzle 20 and located downstream of the first mixer 42 and upstream of the nozzle 20 of the first end effector 16 (FIG. 6). As shown in FIGS. 1 and 3-4, the end effector 16 may include a frame for respectively mounting the first and second mixers 42, 44. Also, the end effector 16 may include a motor 46 for driving both of the mixers 42, 44. For brevity of description, the flexible hose connections between the mixers 42, 44 and the various other electrical wiring have been hidden from view in FIGS. 2 and 3. It is conceivable to have an end effector 16 which does not mount the mixers 42, 44 and motor 46.

The proportioning system 30 may modulate the flow of the A and/or B component. In the present embodiment, for example, the flow rates of the blowing agent and accelerant may be adjusted on the fly in order to alter the strength and density properties of the material. For example, the density and strength properties of the material, between multiple layers or within a given layer, may be adjusted to accommodate a needed void in the mold 24 or a cutout in the mold 24 which is to be subtracted by the milling tool 22. Thereby, a lighter weight material could be used for the majority of the mold 24 and a higher density and strength material may be used in the areas of the mold 24 where the void or cutout is located. For instance, the ECU of the proportioning system 30 may increase or decrease the flow rate of the blowing agent to cause the material being deposited to be of a lower or higher density. This dynamic adjustment of the density and strength of the material via adjusting the accelerant and/or blowing agent as the material is being deposited by the nozzle 20 may guarantee the integrity of the mold 24 after the cutout material is removed by the milling tool 22 in a subsequent step.

In operation, components A and B may be transported to the proportioning system 30. The proportioning system 30 may individually pressurize the components A and B of the material, for example between 150-200 psi, and heat one or both of the components A and B to a specified temperature. The A and B components may also be transported through the hoses to the mixing head 20, where the mixing head 20 mixes the components A and B and forces them down in a desired pattern. The positioning mechanism 12 then maneuvers the end effector 16, according to a preprogramed positioning dataset, to spray the material layer-by-layer. Sufficient time for the material to set in between each pass may be allocated by the positioning mechanism 12. During, before, or after each pass, the proportioning system 30 may include a step of selectively adjusting the blowing agent depending upon a desired density of the material. In this regard, the mold 24 may have differing densities among its various layers. The mold 24 may also have differing densities and strengths among various sections, which are not bound to any particular layer(s). At any time before, during, or after spraying the material the mixing head 20 may purge the component material by using a solvent flush, through the interior parts of mixing head 20 to flush out cured or uncured materials. In doing so the positioning mechanism 12 may purge such materials in a designated area dedicated for waste. Also, prior to depositing each layer, a "waste shot" may be performed to initialize mixing and ensure that the desired characteristics of the material are present. After a specified number of layers of material, the subtractive process may begin. In the embodiment of a single positioning mechanism, the end effector may be rotated to initiate a tool change in order to employ the milling tool 22. In the embodiment of two more positioning mechanisms 12, 14, the mold 24 and/or the positioning mechanism 14 may be moved such that the milling tool 22 of the positioning mechanism 14 may operate on the mold 24. The milling tool 22 may then cut the material to remove sections of the mold 24 or to form a desired pattern, smoothness, or texture (FIG. 7). For example, the milling tool 22 may cut a desired design in the surface of the mold. The desired design may be in the form of a pattern, shape and/or texture. This desired design may be used to mold a corresponding design in a casting material which is subsequently deposited into the mold 24. Thereby, the method may include the additional step of filling the finished mold 24 with a particular casting material. For example, the mold 24 may be filled with concrete in order to mold the concrete into a particular shape or to form an intricate design on the surface of the concrete. Additional support bracing may be provided to prevent deflection when backfilling the 3D printed mold 24 with the casting material. It should be appreciated that the finished 3D printed mold 24 may be backfilled with any desired material.

This layer-by-layer additive and subtraction process may be repeated until the entire 3D printed mold 24 is built according to the specifications of a preprogramed computer model. The mold 24 may uniquely match a desired density pattern for different strengths within the mold 24 which is provided by a preprogramed computer model. The 3D printed mold 24 may also be coated, automatically by the 3D printing system 10 or manually, with various finishing coatings.

The flow rates of the proportioning system 30 may be set from the preprogramed computer model so that the material flow matches the linear track speed of the positioning mechanism(s) 12, 14. As the positioning mechanism 12, 14 speeds up and slows down to add material to the different parts of the mold, the individual ingredient flows may also modulate to match the speed of the position mechanism 12, 14. This allows the printing system to speed up and slow down as needed in order to accommodate various parts (e.g. more complex features) of the preprogrammed model. The material flow rate may follow these needs to add the correct amount of material for each layer or subsection within a given layer.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A three-dimensional printing system, comprising:
   at least one positioning mechanism in the form of at least one robotic arm;
   at least one end effector movably connected to said at least one robotic arm, said at least one end effector including a frame, at least one mixing head in the form of at least one nozzle connected to said frame and configured to dispense a material, a first mixer connected to said frame, a second mixer connected to said frame, a motor connected to said frame and configured for driving said first and second mixers, and at least one subtractive tool configured to subtract at least a portion of said material such that a desired design is achieved; and
   a positioning system mounted to the at least one end effector, wherein the positioning system provides real-time feedback of location of the mixing head.

2. The three-dimensional printing system of claim 1, wherein said at least one mixing head dispenses said material layer-by-layer to form a mold.

3. The three-dimensional printing system of claim 2, wherein said at least one subtractive tool is configured to subtract at least a portion of said material from a surface of said mold such that said desired design is achieved in said surface of the mold.

4. The three-dimensional printing system of claim 1, wherein said material is a plural component material such that said material is composed of at least two components including an activator mixture and a resin mixture.

5. The three-dimensional printing system of claim 4, wherein said mixing head mixes said at least two components and dispenses said material.

6. The three-dimensional printing system of claim 4, further including a proportioning system operably coupled to said at least one mixing head and configured to proportion said at least two components, said proportioning system includes said first and second mixers, and wherein said second mixer is fluidly connected to said at least one nozzle and located downstream of said first mixer and upstream of said at least one nozzle.

7. The three-dimensional printing system of claim 1, wherein the positioning system further provides real-time feedback of flow rate.

8. The three-dimensional printing system of claim 7, wherein the positioning system further provides real-time feedback of current condition.

9. A three-dimensional printing system, comprising:
   a proportioning system configured to proportion a material, said proportioning system includes a first mixer, a second mixer, and a motor configured for driving said first and second mixers:
   a first positioning mechanism in the form of a first robotic arm;
   a second positioning mechanism associated with said first positioning mechanism, the second positioning mechanism being in the form of a second robotic arm;
   a first end effector movably connected to said first robotic arm, said first end effector including a frame and at least one nozzle connected to said frame and operably connected to said proportioning system, said at least one nozzle is configured for dispensing said material layer-by-layer to form a mold, wherein said first mixer is connected to said frame, said second mixer is connected to said frame, and said motor is connected to said frame;
   a second end effector movably connected to said second robotic arm and including at least one subtractive tool which is configured for subtracting at least a portion of said mold; and
   a positioning system mounted to the first end effector, wherein the positioning system provides real-time feedback of location of the at least one nozzle.

10. The three-dimensional printing system of claim 9, wherein said second mixer is fluidly connected to said at least one nozzle and located downstream of said first mixer and upstream of said at least one nozzle.

11. The three-dimensional printing system of claim 10, wherein said material is composed of a first component and a second component such that said first mixer of said proportioning system mixes an accelerant and a blowing agent of said second component, and said second mixer mixes said first component and said second component.

12. The three-dimensional printing system of claim 11, wherein said proportioning system selectively adjusts an amount of said blowing agent depending upon a desired density of the material such that a material density of at least a first portion of a first layer of material is different than a material density of at least a second portion of a second layer of material.

13. The three-dimensional printing system of claim 9, wherein said at least one subtractive tool is configured to subtract at least a portion of material from a surface of said mold such that said desired design is achieved in said surface of the mold.

* * * * *